United States Patent [19]

Wester et al.

[11] Patent Number: 4,765,971
[45] Date of Patent: Aug. 23, 1988

[54] TECHNETIUM (TC-99M)-ARENE COMPLEXES USEFUL IN MYOCARDIAL IMAGING

[75] Inventors: Dennis W. Wester, Florissant; Richard T. Dean, Chesterfield, both of Mo.

[73] Assignee: Mallinckrodt, Inc., St. Louis, Mo.

[21] Appl. No.: 739,511

[22] Filed: May 31, 1985

[51] Int. Cl.$^4$ .............................................. A61K 49/02
[52] U.S. Cl. ......................................... 424/1.1; 424/4; 424/9; 534/14
[58] Field of Search ................... 424/1.1, 9, 4; 534/14

[56] References Cited

U.S. PATENT DOCUMENTS 4,481,184 11/1984 Kronauge et al. .................... 534/14
4,526,724 7/1985 Pillsbury ............................... 534/14

OTHER PUBLICATIONS

Schafer, L., Acta Chem. Scand., vol. 24, No.9, (1970), pp. 3420-3421.
Chem. Abstr. 74:69694z.
Chem. Abstr. 103:42695f.
Chem. Abstr. 96:168787t.
Chem. Abstr. 95:199809k.
Chem. Abst. 89:119837f.

*Primary Examiner*—David M. Naff
*Assistant Examiner*—Stephen C. Wieder
*Attorney, Agent, or Firm*—Bernard, Rothwell & Brown

[57] ABSTRACT

A cationic Tc-99m-arene complex, useful as a myocardial perfusion imaging agent, is produced by reacting a Tc compound in an oxidation state higher than I with benzene or substituted benzene in the presence of a reducing agent and a metal halide which is capable of withdrawing halide ions.

39 Claims, No Drawings

TECHNETIUM (TC-99M)-ARENE COMPLEXES USEFUL IN MYOCARDIAL IMAGING

BACKGROUND OF THE INVENTION

1. Field of the Invention

This invention relates to methods of preparing cationic complexes of Tc-99m which are useful as myocardial imaging agents and to novel compositions containing Technetium-99m complexes.

2. Prior Art

Diagnostic nuclear medicine involves the administration to a subject of a radiation-emitting isotope which localizes in the tissues of interest. An image of these tissues is then obtained using a scintillation camera such as an Anger scintillation camera. Tc-99m is an ideal radioisotope for use in nuclear medicine. It has a half-life of 6 hours and a gamma-radiation of 140 keV, with no alpha or beta radiation. It is easily prepared using a Mo-99/Tc-99m generator and it is relatively inexpensive. Finally, its chemistry is such that it can be incorporated into diverse chemical forms in order to image different types of tissues.

Tc-99m has become widely used for scintillation scanning of bone tissue and infarcted myocardial tissue. In these applications, the Tc-99m is administered with a carrier such as methanehydroxydiphosphonate and a reducing agent such as $SnCl_2$. The Tc-99m-diphosphonate complex acts as a calcium-seeking agent which accumulates in bone, particularly at sites of high calcium turnover in newly forming or cancerous bone, and in myocardial infarcts that contain calcium phosphate.

Within the past several years, interest has developed in producing Tc-99m-based radiodiagnostic agents which will accumulate in normal heart tissue, as opposed to infarcted tissue. Such radiodiagnostic agents would be of great benefit inasmuch as they would allow for the early identification of individuals at high risk of having heart attacks. Deutsch and coworkers determined that the cationic Tc-99m complex $[^{99m}Tc(dmpe)_2Cl_2]^+$, where dmpe is bis(1,2-dimethylphosphino)ethane, accumulated in normal dog heart tissue, allowing gamma-ray images to be taken (Science, 214:85–86 [1981]).

Several additional Tc-99m cationic complexes have been described of interest for studies dealing with the imaging of normal heart tissue. Most prominent have been $[^{99m}Tc(dmpe)_3]^+$, Gerson, M. C., Deutsch, E. A., et al., Eur. J. Nuc. Med., 9:403 [1984] and $[^{99m}Tc(tBuNC)_6]^+$, Jones, A. G., et al., Int. J. Nucl. Med. Biol., 11:225 [1984]; Jones, A. G., Davidson, A., Abrams, A. J., U.S. Pat. No. 4,452,774. Clinical imaging with these agents is less than optimal. Therefore, a need still exists for additional Tc-99m complexes which will accumulate preferentially in heart tissue.

Technetium-arene complexes have received only cursory attention in the literature, usually being prepared for comparative studies with analogous manganese or rhenium compounds. The preparations of cyclopentadienyl and benzene derivatives were reported as early as 1961 (Huggins, D. K. and Kaesz, H. D., J. Amer. Chem. Soc., 83:4474 [1961]; Fischer, E. O. and Schmidt, M. W., Chem. Ber., 100:3782 [1967]; Baumgartner, F. et al., Chem. Ber., 94:2198 [1961]; Palm, C. et al., Tet. Lett., 1962(6) 253). Preparation of a hexamethylbenzene derivative was described by Fischer, E. O. and Schmidt, M. W., Chem. Ber., 102:1954 (1969). Since that time the compounds have received no further attention in the literature.

The benzene and hexamethylbenzene complexes are sandwich-type compounds in which a technetium(I) atom is II-bonded to two arenes, giving a cationic complex. Synthetic routes to the benzene and hexamethylbenzene complexes of Tc-99, as reported in the prior art, are long and involved, making them unacceptable for commercial use. The prior art procedures generally use $TcCl_4$ as the starting material, a substance which is not easily prepared from the $NaTcO_4$ obtained from Mo-99/Tc-99m generators. In the prior art procedures, $TcCl_4$ and benzene or hexamethylbenzene (along with other reagents) are heated in a sealed tube for 3 days or 24 hours, respectively. Since the half-life of Tc-99m is 6 hours, it is apparent that most of the Tc-99m obtained from a generator will have decayed into non-radioactive Tc-99 in the time required to prepare a technetium-arene complex by the prior art processes. Accordingly, it is not possible to prepare Tc-99m-arene complexes having desirably high ratios of Tc-99m/Tc-99 which are practically useful as radiodiagnostics using the procedures of the prior art.

SUMMARY OF THE INVENTION

The present invention provides an efficient method for preparing Tc-99m-arene complexes useful as radiodiagnostic agents. In accordance with the method of the invention, a mixture comprising a Tc-99m compound in an oxidation state higher than I; a reducing agent; a metal halide which is capable of withdrawing halo ions; and benzene or substituted benzene is reacted to produce the desired complex. The method of the invention results in the production of a composition comprising compounds of the formula

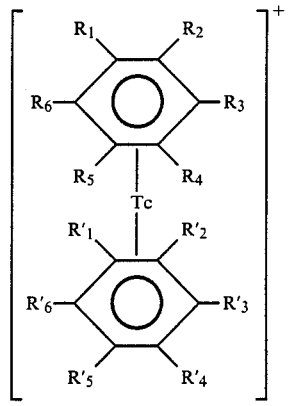

wherein Tc is an atom of Tc-99m or Tc-99 in an oxidation state of I, $R_{1-6}$ and $R'_{1-6}$ are each, individually, hydrogen or a substituent selected from the group consisting of alkyl, alkenyl, alkynyl, fluoroalkyl and haloalkenyl having up to 12 carbon atoms; halo; carbamoyl; amido; amino; acyl; acyloxy; cyano; alkoxy; alkoxyalkyl; ester groups; keto groups; and aldehyde groups, provided that the number of halo atoms directly substituted on the two rings does not exceed three, or pharmaceutically acceptable salts thereof.

Due to the rapidity of the method of the invention, it is possible to prepare compositions in which at least about 3 mol. % of the Tc atoms in the composition are in the form of radioactive Tc-99m, that is, they have not undergone decay to Tc-99. Such compositions, which were impossible to produce using prior art methods, are particularly well suited for use as myocardial perfusion imaging agents, since they exhibit levels of gamma emission which give excellent scintigraphic images.

There is also provided, in accordance with the present invention, a method for imaging myocardial tissue which comprises intravenously administering to a host a composition produced by the method of the invention, together with a parenteral carrier material; allowing Tc-99m to accumulate in the myocardial tissue; and imaging the myocardial tissue containing the Tc-99m with a scintigraphic camera.

DETAILED DESCRIPTION OF THE INVENTION

The method of the invention produces a composition for use in myocardial imaging which comprises compounds of the formula

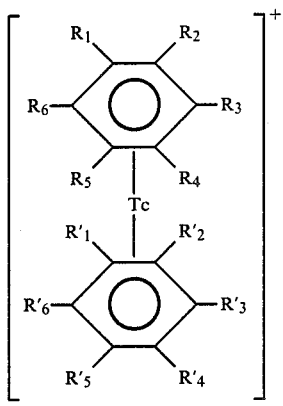

wherein Tc is an atom of Tc-99m or Tc-99 in an oxidation state of I, $R_{1-6}$ and $R'_{1-6}$ are each, individually, hydrogen or a substituent selected from the group consisting of alkyl, alkenyl, alkynyl, fluoroalkyl and haloalkenyl having up to 12 carbon atoms; halo; carbamoyl; amido; amino; acyl; acyloxy; cyano; alkoxy; alkoxyalkyl; ester groups; keto groups; and aldehyde groups, provided that the number of halo atoms directly substituted on the two rings does not exceed three, or pharmaceutically acceptable salts thereof.

Preferred compounds are those in which $R_{1-6}$ and $R'_{1-6}$ are each, individually, hydrogen or alkyl such that the total number of carbon atoms in the alkyl substituents on the two rings is from 4 to 24 and most preferably from 6 to 12. As used herein, the terms alkyl and alkenyl include groups which are straight-chain, branched-chain, bridged or cyclic.

In the complex described by the above formula, the Tc(I) atom is II-bonded to the two arene groups. The technetium complex can be in the form of a pharmaceutically acceptable salt, e.g., a salt formed with a pharmaceutically acceptable anion such as chloro or other halogens, phosphate, citrate or acetate.

In the composition of the invention, some of the Tc will be in the form of the isotope Tc-99m and some will be in the form of Tc-99, which results from gamma decay of the Tc-99m. A major advantage of the method of the invention is that the rapidity of the reaction allows the preparation of compositions in which at least about 3 mol. % of the Tc is in the form of the Tc-99m isotope. The method is also useful, however, in producing compositions having lower and higher levels of Tc-99m. The ability to produce compositions having high concentrations of Tc-99m depends not only on the reaction time required to produce the technetium-arene complex, but also on the ratio of Tc-99m to Tc-99 in the starting material. As those skilled in the art are aware, this ratio is dependent on the time interval between elutions of the Mo-99/Tc-99m column used to generate the technetium starting material. Using synthetic procedures of the prior art to produce the technetium-arene complexes, the highest concentration of Tc-99m one could reasonably be expected to produce would be on the order of 2.5 mol. %. This assumes that the generator is eluted at 1 hr. intervals (thereby producing a starting material having a high Tc-99m/Tc-99 ratio), a practice which would be unusual in actual usage.

As previously indicated, the cationic technetium complex is produced by reacting a mixture containing a Tc-99m compound in an oxidation state higher than I; a reducing agent; a metal halide which is capable of withdrawing a halide ion from technetium; and benzene or substituted benzene. The Tc-99m compound used as a starting material can be any compound in which the Tc-99m is in a higher oxidation state than I such as the IV or VII oxidation state. Most commonly, the starting material will be $^{99m}TcCl_4$ or $Na^{99m}TcO_4$. $Na^{99m}TcO_4$ is generally preferred because it is readily available and easily produced using commercially available Mo-99/Tc-99m generators.

The reducing agent is any known reducing agent which is capable of reducing Tc-99m in a higher oxidation state such as the Tc-99m(IV) or Tc-99m(VII) to Tc-99m(I) and which does not interfere with the formation of the technetium-arene complex. Preferably, the reducing agent is selected from the group consisting of Al, Zn, Fe and Sn. Most preferably, the reducing agent employed in the reaction is aluminum powder. We have found that zinc is capable of driving the reaction, although the yield is somewhat lower than that obtained using aluminum. The yield was found to vary as a function of the particle size of the zinc, the yield using 30 mesh zinc being lower than −200 mesh, which in turn is lower than zinc dust. The reducing agent is provided to the reaction mixture in a large molar excess to the amount of technetium compound present.

The metal halide is any compound which has the ability to remove halide ions from technetium. Preferred metal halides for this purpose are compounds of the formula $AlX_3$, wherein X is halogen, preferably Cl or Br. $AlX_3$ can be added directly to the reaction mixture or it can be formed in situ by providing appropriate amounts of aluminum powder and the corresponding HX compound, e.g., HCl or HBr. Other suitable metal halides for use in the method of the invention include the chloride salts of zinc, iron and tin. It is believed that the metal halide serves as a halide ion acceptor and is essential to the reaction in order to attract halide away from technetium by the formation of tetrachloroaluminate. When the starting material is $TcCl_4$, the need for a halide acceptor is readily apparent. For $NaTcO_4$, we have found that the metal halide compound is still required. While not wishing to be bound by any particular theory of the reactiob mechanism, it is believed that the pertechnetate undergoes an initial chlorination step, followed by reduction to the Tc(I) oxidation state and subsequent or simulteneous dechlorination. The amount of metal halide employed is generally in large molar excess to the amount of technetium compound employed in the reaction, e.g., at least about 10 times the amount of technetium on a molar basis.

Isomerization of the methylbenzenes may occur in the presence of aluminum chloride. For example, when starting with pentamethylbenzene, both tetramethyl- and hexamethylbenzene are found in the reaction mixture in substantial amounts, indicating isomerization of methyl groups during the reaction. The degree of isomerization was virtually independent of the amount of $AlCl_3$ present. Equilibrium mixtures of methylbenzenes were formed using as little as 1 mg of $AlCl_3$ in 2 ml of the substituted benzene. Isomerization occurs in the presence of aluminum powder and HCl as well. In the presence of zinc and HCl, the isomerization has not been observed. Thus, the addition of zinc and HCl is preferred for the formation of the tri- and tetramethyl-benzene compounds where different isomers may result, e.g., 1,2,3,4-$C_6H_2(CH_3)_4$ may isomerize to 1,2,3,5-$C_6H_2(CH_3)_4$.

The benzene or substituted benzene is provided to the reaction mixture in a large molar excess to the amount of the technetium compound. Preferably, the benzene or substituted benzene is provided to the reaction mixture in an amount of at least about 100 moles per mole of technetium compound. The substituents which can be present on the benzene are any of the substituents defined above as $R_{1-6}$ and $R'_{1-6}$.

When benzene or a substituted benzene that is liquid at the reaction temperature is employed, the reaction can generally be carried out in the absence of solvent. Where a solvent is required, any solvent which is inert to the reactants and does not interfere with the reaction can be employed. Cyclohexane and hexafluorobenzene are preferred solvents. $AlBr_3$ can be employed both as the metal halide (halide acceptor) and solvent; however, it is not preferred as a solvent inasmuch as unacceptable amounts of aluminum tend to be found in the product.

The reaction can be carried out in any suitable sealed reaction vessel, which is advantageously provided with means for stirring the reactants and for controlling the temperature of the reactants. The reaction can be carried out at temperature from about 100° C. to about 150° C., preferably from about 130° C. to 140° C. and most preferably at about 135° C. Reaction time is generally not more than about 90 min. and is preferably from about 40 min. to 50 min. The product can be recovered by means which are conventional in the art, e.g., by extracting the product into an aqueous phase from the reaction mixture and filtering insoluble impurities from the aqueous phase containing the product.

The composition which is obtained by the method of the invention can be employed as a myocardial perfusion imaging agent using techniques known in the art. The composition, together with a parenteral carrier material, is injected intravenously to a subject in an amount sufficient to yield a good scintigraphic image. Generally, an amount sufficient to provide from about 30 $\mu$Ci to about 150 $\mu$Ci per kilogram of body weight is administered to the subject. After a sufficient period of time has passed for Tc-99m to accumulate in myocardial tissues (usually about 5 to 240 min. post-injection), an image is obtained using a conventional scintigraphic camera. Typical parenteral carrier materials include sterile saline solutions buffered to about 7 pH, which may contain any pharmaceutical adjuvants normally present in injectable solutions.

The following examples are intended to illustrate further the practice of the invention and are not intended to limit its scope in any way.

EXAMPLE 1

Preparation of Reconstituted $Na^{99m}TcO_4$

Generator eluent (a dilute [1.9–190 ng/ml] solution of $Na^{99m}TcO_4$ in normal saline) from a commercial Tc-99m generator (Mallinckrodt Ultra-Technekow FM), was placed in a one-necked 1000-ml round-bottomed flask and taken to dryness on a rotary evaporator with a bath at 50° C. The solid was washed with acetone, the acetone evaporated to dryness, the solid was washed with acetone and dried again and finally washed with 10 ml acetone to give "reconstituted $NaTcO_4$", a dilute solution of $Na^{99m}TcO_4$ in acetone, nearly free from NaCl from the normal saline.

EXAMPLE 2

Preparation of $^{99m}Tc[C_6H(CH_3)_5]_2{}^+Cl^-$

Reconstituted $Na^{99m}TcO_4$ (1 ml) was placed in a 10 ml serum vial sealed with a Teflon ®-coated stopper and aluminum closure, evaporated to dryness under vacuum and equilibrated with argon gas (1 atm.). The argon was pumped away, the vial was refilled with argon (1 atm.), the argon again was pumped away, and finally the vial was filled with argon (1 atm.) for a third time. In a glove bag under argon, the vial was opened. A miniature Teflon ®-coated stir bar, Al powder (−40 mesh, 20 mg), $AlCl_3$ (10 mg), $C_6H(CH_3)_5$ (pentamethylbenzene, 100 mg) and $C_6F_6$ (hexafluorobenzene, 2 ml) were added to the vial. The vial was sealed with a Teflon ®-coated stopper and aluminum closure, heated in an oil bath at 135° C. for 60 min. and cooled slowly to 0° C. in an ice bath. The vial was opened and cold water (1.5 ml) was added. After restoppering and shaking vigorously for 15 sec., the vial was set aside, whereupon the aqueous layer separated. The aqueous layer was pipetted into a centrifuge tube and was centrifuged for 5 min. The aqueous layer was then filtered through filter paper. A second portion of water (1.5 ml) was added to the original organic layer and mixed thoroughly by shaking. The aqueous layer was separated, centrifuged and filtered as before, the filtrates being combined to give a solution of the crude product.

Analysis by high pressure liquid chromatography (HPLC) showed the presence of several compounds in the crude product. A PRP-1 (Hamilton, 250×4.1 mm, 10$\mu$) reversed phase analytical column was eluted with a mobile phase consisting of 38% ethanol, 62% $H_2O$ and 2 mM $KH_2PO_4$ buffered to a pH of 3.5 with $H_3PO_4$ and flowing at 0.75 ml/min. The compounds in the product were identified on the basis of retention time as (tetramethylbenzene)(pentamethylbenzene)technetium(I), bis(pentamethylbenzene)technetium(I) and (pentamethylbenzene)(hexamethylbenzene)technetium(I). Gas chromatography (GC) of the organic layer showed in addition to pentamethylbenzene, substantial amounts of tetramethylbenzene and hexamethylbenzene, both of which are produced during the reaction through the catalytic effect of aluminum chloride.

EXAMPLE 3

Preparation of $^{99m}Tc[C_6H(CH_3)_5]_2{}^{+Cl-}$

Reconstituted $Na^{99m}TcO_4$ (1 ml) was placed in a 10 ml vial and evaporated to dryness under vacuum. The vial was opened and a miniature Teflon ®-coated stir bar, aluminum powder (−40 mesh, 50 mg) and $C_6H(CH_3)_5$ (pentamethylbenzene, 1 g) were added. The mixture was purged with HCl gas (technical grade) for 1 min. and the vial then was stoppered with a Teflon ®-coated stopper under HCl flow and sealed with a closure. The vial was heated at 135° C. in an oil bath for 90 min., cooled to 0° C. in an ice bath and opened. Cold water (1.5 ml) and ethylether (2.0 ml) were added and the mixture was shaken vigorously. After settling, the aqueous layer was separated, placed in a centrifuge tube and centrifuged for 5 min. The aqueous layer was filtered through filter paper. To the original organic layer in the vial was added another portion of cold $H_2O$ and the extraction and filtration procedure was repeated, the filtrates being combined to give a solution of the crude product.

Analysis of the crude product by HPLC showed the presence of several compounds. A PRP-1 (Hamilton, 250×4.1 mm, 10 u) reversed phase analytical column was eluted with a mobile phase consisting of 38% ethanol, and 62% $H_2O$ and 2 mM $KH_2PO_4$ buffered to a pH of 3.5 and flowing at 0.75 ml/min. The compounds in the product were identified by their retention times as being (tetramethylbenzene)(pentamethylbenzene)technetium(I), bis(pentamethylbenzene)technetium(I) and (pentamethylbenzene)(hexamethylbenzene)technetium(I). GC of the organic layer showed the presence of tetramethylbenzene, pentamethylbenzene and hexamethylbenzene, a result of the catalytic effect of aluminum chloride.

EXAMPLE 4

Preparation of $^{99m}Tc[1,2,3,4-C_6H_2(CH_3)_4]_2^+Cl^-$

Reconstituted $Na^{99m}TcO_4$ (1 ml) was placed in a 10 ml vial and evaporated to dryness under vacuum. To the vial were added a miniature Teflon ®-coated stir bar, $1,2,3,4-C_6H_2(CH_3)_4$ (tetramethylbenzene, 2 ml) and Zn powder (−200 mesh, 10 mg). The mixture was purged with HCl gas (technical grade) for 15 sec. The vial was stoppered with a Teflon ®-coated stopper under HCl flow and sealed with a closure. The vial was heated at 135° C. in an oil bath for 90 min., cooled to 0° C. in an ice bath and opened. Cold water (1.5 ml) was added, the mixture was shaken vigorously and the aqueous layer was separated, placed in a centrifuge tube and centrifuged for 5 min. The aqueous layer was filtered through a membrane filter (Millex FG). Another portion of cold water (1.5 ml) was added to the original organic layer and the extraction and filtration procedure was repeated (using the same filter). The filtrates were combined to give a solution of crude product.

Analysis of the crude product by HPLC showed the presence of two compounds. A PRP-1 (Hamilton, 250×4.1 mm, 10 u) reversed phase analytical column was eluted with a mobile phase consisting of 38% ethanol, and 62% $H_2O$ and 2 mM $KH_2PO_4$ buffered to a pH of 3.5 and flowing at 0.75 ml/min. The major peak (70%) was identified as being bis(1,2,3,4-tetramethylbenzene)technetium(I) on the basis of its retention time. GC of the organic layer showed the presence of 1,2,3,4- and a trace of 1,2,3,5-tetramethylbenzene, essentially identical to a gas chromatogram of the starting material $1,2,3,4-C_6H_2(CH_3)_4$.

EXAMPLE 5

Biodistribution of $^{99m}Tc[C_6(CH_3)_6]_2^+$ in Rats at 5 min.

A sample of $^{99m}Tc[C_6(CH_3)_6]_2^+$ was prepared by the method of Example 3, with the exception that $C_6(CH_3)_6$ (500 mg) and $C_6H_{12}$ (cyclohexane, 2 ml) were substituted for the $C_6H(CH_3)_5$. The sample consisted of the HPLC fraction containing the technetium complex (mobile phase: 38% ethanol, 62% $H_2O$ and 2 mM $KH_2PO_4$ buffered to a pH of 3.5) diluted to an activity of 13.2 μCi/ml with normal saline.

Sprague Dawley rats (4 females, weight 193–210 g) were injected with ∼25 μCi/kg of the $^{99m}Tc[C_6(CH_3)_6]_2^+$ sample through a lateral tail vein. At five min. post-injection, the rats were sacrificed by cervical dislocation and tissue samples were weighed and assayed for radioactivity. The results are reported in Table 1 as a mean % dose/g or ml of tissue.

EXAMPLE 6

Biodistribution of $^{99m}Tc[1,3,5-C_6H_3(CH_3)_3]_2^+$ in Rats at 5 min.

A sample of $^{99m}Tc[1,3,5-C_6H_3(CH_3)_3]_2^+$ was prepared by the method of Example 3 with the exception that $1,3,5-C_6H_3(CH_3)_3$ (2 ml) was substituted for the $C_6H(CH_3)_5$. The sample consisted of the HPLC fraction containing the technetium complex (mobile phase: 38% ethanol, 62% $H_2O$ and 2 mM $KH_2PO_4$ buffered to a pH of 3.5) diluted to an activity of 12 μCi/ml with normal saline.

Biodistribution studies were carried out using a procedure identical to that of Example 5. Results are reported in Table 1.

TABLE 1

| Tissue | Mean % Dose/g or ml Tissue at 5 Min. after Intravenous Administration | |
|---|---|---|
|  | $^{99m}Tc[C_6(CH_3)_6]_2^+$ | $^{99m}Tc[1,3,5-C_6H_3(CH_3)_3]_2^+$ |
| Heart | 3.74 | 2.06 |
| Blood | 0.21 | 0.08 |
| Liver | 0.58 | 0.73 |
| Lung | 1.58 | 0.95 |
| Kidney | 8.83 | 8.20 |
| Muscle | 0.62 | 0.40 |
| Brain | 0.04 | 0.02 |

EXAMPLE 7-10

Using procedures similar to those described in Examples 1–4, the compounds $^{99m}Tc[1,2,3,5-C_6H_2(CH_3)_4]_2^+$, $^{99m}Tc[1,2,4,5-C_6H_2(CH_3)_4]_2^+$, $^{99m}Tc[1,2,3-C_6H_3(CH_3)_3]_2^+$ and $^{99m}Tc[1,2,4-C_6H_3(CH_3)_3]_2^+$ were prepared using $1,2,3,5-C_6H_2(CH_3)_4$, $1,2,4,5-C_6H_2(CH_3)_4$, $1,2,3-C_6H_3(CH_3)_3$ and $1,2,4-C_6H_3(CH_2)_3$, respectively, as starting materials.

What is claimed is:

1. A composition comprising compounds of the formula:

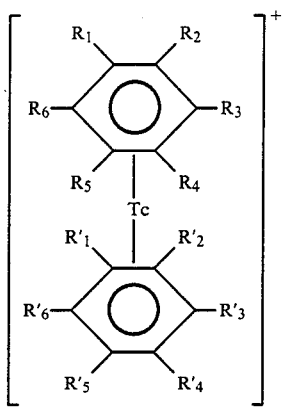

wherein Tc is an atom of Tc-99m or Tc-99 in an oxidation state of I, $R_{1-6}$ and $R'_{1-6}$ are each, individually, hydrogen or a substituent selected from the group consisting of alkyl, alkenyl, alkynyl, fluoroalkyl and haloalkenyl having up to 12 carbon atoms; halo; carbamoyl; amido; amino; acyl; acyloxy; cyano; alkoxy; alkoxyalkyl; ester groups; keto groups; and aldehyde groups, provided that the number of halo atoms directly substituted on the two rings does not exceed three, or pharmaceutically acceptable salts thereof, provided that at least about 3 mol % of the Tc(I) atoms are in the isotopic form Tc-99m.

2. A composition as claimed in claim 1 which contains the compound $^{99m}Tc[C_6H(CH_3)_5]_2{}^+$ or a pharmaceutically acceptable salt thereof.

3. A composition as claimed in claim 1 which contains the compound $^{99m}Tc[C_6H(CH_3)_5]_2{}^+Cl^-$.

4. A composition as claimed in claim 1 which contains the compound $^{99m}Tc[1,2,3,4-C_6H_2(CH_3)_4]_2{}^+$ or a pharmaceutically acceptable salt thereof.

5. A composition as claimed in claim 1 which contains the compound $^{99m}Tc[1,2,3,4-C_6H_2(CH_3)_4]_2{}^+Cl^-$.

6. A composition as claimed in claim 1 which contains the compound $^{99m}Tc[1,3,5-C_6H_3(CH_3)_3]_2{}^+$ or a pharmaceutically acceptable salt thereof.

7. A composition as claimed in claim 1 which contains the compound $^{99m}Tc[C_6(CH_3)_6]_2{}^+$ or a pharmaceutically acceptable salt thereof.

8. A composition as claimed in claim 1 which contains the compound $^{99m}Tc[1,2,3,5-C_6H_2(CH_3)_4]_2{}^+$ or a pharmaceutically acceptable salt thereof.

9. A composition as claimed in claim 1 which contains the compound $^{99m}Tc[1,2,4-C_6H_3(CH_3)_3]_2{}^+$ or a pharmaceutically acceptable salt thereof.

10. A method of producing a cationic Tc(I)-99/99m-arene complex useful as a myocardial perfusion imaging agent which comprises:
   (a) eluting $Na^{99m}TcO_4$ from a Tc-99m generator; and
   (b) reacting the $Na^{99m}TcO_4$ with benzene or benzene substituted by one or more substituents each selected from the group consisting of alkyl, alkenyl, alkynyl, fluoroalkyl and haloalkenyl having up to 12 carbon atoms; halo; carbamoyl; amido; amino; acyl; acyloxy; cyano; alkoxy; alkoxyalkyl; ester groups; keto groups; and aldehyde groups,
with the reactants being in contact with a reducing agent and a metal halide which is capable of withdrawing halide ions from technetium.

11. A method as claimed in claim 10, wherein the reducing agent is aluminum and the metal halide is $AlCl_3$.

12. A method as claimed in claim 10, wherein the reducing agent is zinc and the metal halide is zinc chloride.

13. A method as claimed in claim 10, wherein $Na^{99m}TcO_4$ is reacted with pentamethylbenzene.

14. A method as claimed in claim 10, wherein $Na^{99m}TcO_4$ is reacted with 1,2,3,4-tetramethylbenzene.

15. A method as claimed in claim 10, wherein $Na^{99m}TcO_4$ is reacted with hexamethylbenzene.

16. A method as claimed in claim 10, wherein $Na^{99m}TcO_4$ is reacted with 1,3,5-trimethylbenzene.

17. A method as claimed in claim 10, wherein $Na^{99m}TcO_4$ is reacted with 1,2,3,5-tetramethylbenzene.

18. A method as claimed in claim 10, wherein $Na^{99m}TcO_4$ is reacted with 1,2,4-trimethylbenzene.

19. A method of imaging myocardial tissue which comprises intravenously administering to a subject a composition comprising the composition of claim 1 and a parenteral carrier material, allowing Tc-99m to accumulate in the myocardial tissue and imaging the myocardial tissue with a scintigraphic camera.

20. A method of imaging myocardial tissue which comprises intravenously administering to a subject a composition comprising the composition of claim 2 and a parenteral carrier material, allowing Tc-99m to accumulate in the myocardial tissue and imaging the myocardial tissue with a scintigraphic camera.

21. A method of imaging myocardial tissue which comprises intravenously administering to a subject a composition comprising the composition of claim 3 and a parenteral carrier material, allowing Tc-99m to accumulate in the myocardial tissue and imaging the myocardial tissue with a scintigraphic camera.

22. A method of imaging myocardial tissue which comprises intravenously administering to a subject a composition comprising the composition of claim 4 and a parenteral carrier material, allowing Tc-99m to accumulate in the myocardial tissue and imaging the myocardial tissue with a scintigraphic camera.

23. A method of imaging myocardial tissue which comprises intravenously administering to a subject a composition comprising the composition of claim 5 and a parenteral carrier material, allowing Tc-99m to accumulate in the myocardial tissue and imaging the myocardial tissue with a scintigraphic camera.

24. A method of imaging myocardial tissue which comprises intravenously administering to a subject a composition comprising the composition of claim 6 and a parenteral carrier material, allowing Tc-99m to accumulate in the myocardial tissue and imaging the myocardial tissue with a scintigraphic camera.

25. A method of imaging myocardial tissue which comprises intravenously administering to a subject a composition comprising the composition of claim 7 and a parenteral carrier material, allowing Tc-99m to accumulate in the myocardial tissue and imaging the myocardial tissue with a scintigraphic camera.

26. A method of imaging myocardial tissue which comprises intravenously administering to a subject a composition comprising the composition of claim 8 and a parenteral carrier material, allowing Tc-99m to accumulate in the myocardial tissue and imaging the myocardial tissue with a scintigraphic camera.

27. A method of imaging myocardial tissue which comprises intravenously administering to a subject a composition comprising the composition of claim 9 and a parenteral carrier material, allowing Tc-99m to accumulate in the myocardial tissue and imaging the myocardial tissue with a scintigraphic camera.

28. A compound of the formula $^{99m}Tc[C_6H(CH_3)_5]_2^+$ or a pharmaceutically acceptable salt thereof.

29. The compound $^{99m}Tc[C_6H(CH_3)_5]_2^+Cl^-$.

30. A compound of the formula $^{99m}Tc[1,2,3,4-C_6H_2(CH_3)_4]_2^+$ or a pharmaceutically acceptable salt thereof.

31. The compound $^{99m}Tc[1,2,3,4-C_6H_2(CH_3)_4]_2^+Cl^-$.

32. A compound of the formula $^{99m}Tc[1,3,5-C_6H_3(CH_3)_3]_2^+$ or a pharmaceutically acceptable salt thereof.

33. A compound of the formula $^{99m}Tc[1,2,3,5-C_6H_2(CH_3)_4]_2^+$ or a pharmaceutically acceptable salt thereof.

34. A compound of the formula $^{99m}Tc[1,2,4-C_6H_3(CH_3)_3]_2^+$ or a pharmaceutically acceptable salt thereof.

35. A compound of the formula $^{99m}Tc[1,2,4,5-C_6H_2(CH_3)_4]_2^+$ or a pharmaceutically acceptable salt thereof.

36. A compound of the formula $^{99m}Tc[1,2,3-C_6H_3(CH_3)_3]_2^+$ or a pharmaceutically acceptable salt thereof.

37. A composition as claimed in claim 1, wherein $R_{1-6}$ and $R'_{1-6}$ are each, individually selected from the group consisting of hydrogen and alkyl, provided the total number of carbon atoms in the alkyl substituents on the two rings is from 4 to 24.

38. A composition as claimed in claim 1, wherein $R_{1-6}$ and $R'_{1-6}$ are each, individually selected from the group consisting of hydrogen and alkyl, provided the total number of carbon atoms in the alkyl substituents on the two rings is from 6 to 12.

39. A method as claimed in claim 10, wherein the metal halide is formed in situ by providing appropriate amounts of aluminum powder and either hydrogen chloride or hydrogen bromide.

* * * * *

UNITED STATES PATENT AND TRADEMARK OFFICE
CERTIFICATE OF CORRECTION

PATENT NO. : 4,765,971

DATED : Aug. 23, 1988

INVENTOR(S) : Wester et al.

It is certified that error appears in the above-identified patent and that said Letters Patent is hereby corrected as shown below:

Column 4, line 62, "reactiob" should be --reaction--;

Column 4, line 66, "simulteneous" should be --simultaneous--.

Column 8, line 54, "EXAMPLE" should be --EXAMPLES--.

Column 9, line 67, after "technetium" insert the following:

--to produce said complex, wherein at least about 3 mol. % of the Tc(I) atoms are in the isotopic form Tc-9m,--

Signed and Sealed this

Thirteenth Day of February, 1990

*Attest:*

JEFFREY M. SAMUELS

*Attesting Officer*     *Acting Commissioner of Patents and Trademarks*